United States Patent [19]

King

[11] 4,086,140
[45] Apr. 25, 1978

[54] PROCESS FOR ISOLATING FIBRINOLYTIC SUBSTANCES

[76] Inventor: John Burnham King, Sandown Lodge, Glebe Rd., Rondebosch, Cape, South Africa

[21] Appl. No.: 801,348

[22] Filed: May 27, 1977

Related U.S. Application Data

[62] Division of Ser. No. 628,006, Nov. 3, 1975, Pat. No. 4,039,658, which is a division of Ser. No. 347,254, Apr. 2, 1973, abandoned.

[30] Foreign Application Priority Data

Apr. 5, 1972 South Africa ............... 72/2311

[51] Int. Cl.² ........................................... C07G 7/026
[52] U.S. Cl. ............................................. 195/66 B
[58] Field of Search ................................ 195/66 B

[56] References Cited

U.S. PATENT DOCUMENTS 3,657,416  4/1972  Reid et al. .............................. 424/94
3,713,981  1/1973  Broadbent et al. ..................... 195/62

OTHER PUBLICATIONS

Katsuki et al., Chemical Abstracts, Oct. 1962, vol. 57, 8881h.

Primary Examiner—Lionel M. Shapiro
Attorney, Agent, or Firm—Omri M. Behr

[57] ABSTRACT

A new fibrinolytic enzymatic product having also anticoagulant properties is recovered from bile. It can be further purified to yield several fractions, all having similar activities, their molecular weights varying between about 5,000 and 50,000. The product or its fibrinolytically active derivatives are used to dissolve fibrin and inhibit blood coagulation in vivo or in vitro.

6 Claims, 3 Drawing Figures

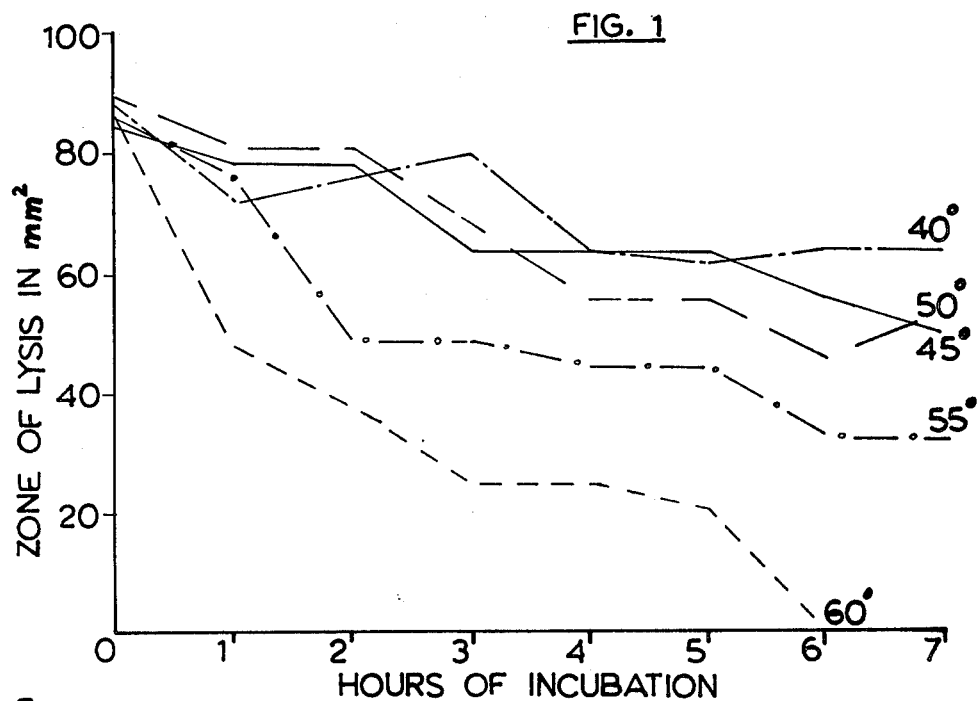
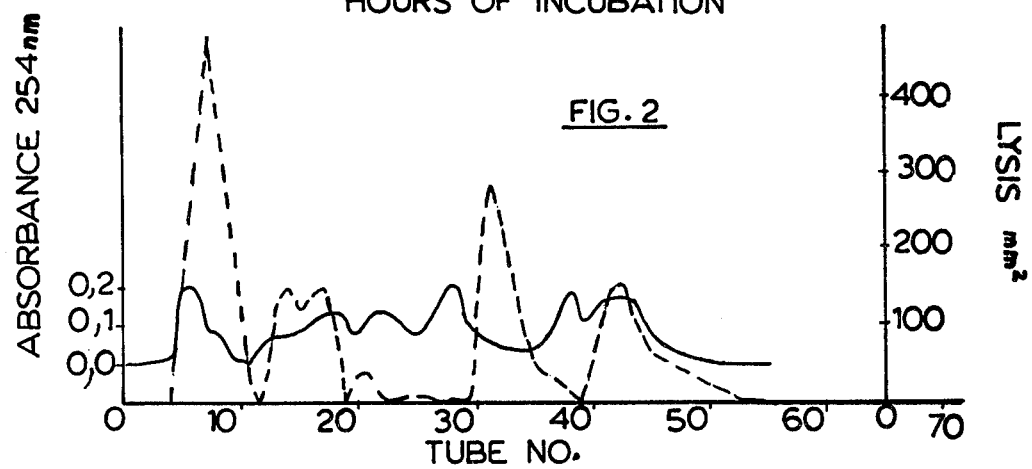
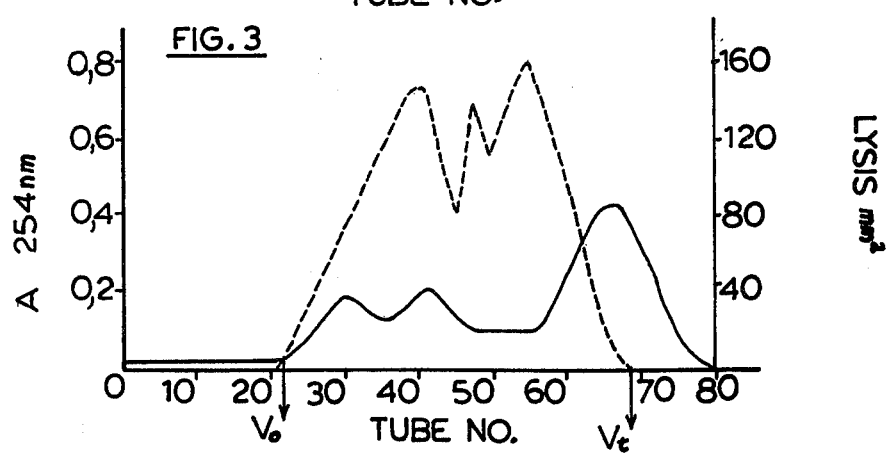

PROCESS FOR ISOLATING FIBRINOLYTIC SUBSTANCES

This is a division of application Ser. No. 628,006, filed Nov. 3, 1975 now U.S. Pat. No. 4,039,658 which is a division of application Ser. No. 347,254 filed Apr. 2, 1973, now abandoned.

BACKGROUND OF THE INVENTION

The present invention relates to improvements in fibrinolytic substances.

The coagulation of fibrinogen in blood results in fibrin clots, that is to say blood clots. Whilst the clotting of blood is necessary to stop the bleeding of wounds, it gives rise to thrombosis if blood clots are formed inside the circulatory system. Substances are known, some of which can be administered therapeutically which inhibit the formation of fibrin clots, e.g. heparin or the active principle of the venom of the Malayan pit viper. Most of these substances are either ineffective or at best weakly effective in dissolving fibrin clots once they have formed, and they can give rise to dangerous side effects. An enzyme, plasmin, will dissolve clots, but the normal plasmin concentration in human blood is too low to be effective in the short term. Plasmin formation can be stimulated by the administration of a protein substance, streptokinase, but this product is very expensive and not without side effects. Other substances are so exorbitantly expensive as to be of purely academic interest. Accordingly three exists a clear need for new substances having fibrinolytic activity, i.e., the property of dissolving blood clots, even if they are advantageous by comparison with the prior art in even one of the aforesaid respects. Such substances, would also be of value for laboratory purposes.

For many purposes such substances would be even more useful if in addition they had the property of inhibiting clot formation.

The present invention is based on the discovery of a new fibrinolytic substance or group of substances in bile.

SUMMARY OF THE INVENTION

In accordance with the invention there is provided in a form more concentrated and/or purified than its natural occurrence a fibrinolytic substance having in addition to its fibrinolytic activity the following characteristics:

(i) It occurs in mammalian bile and can be recovered therefrom, after removal of interfering bile acids if present, by precipitation with ammonium sulphate and further purification by exclusion chromatography on cross-linked polydextran suitable for the separation of proteins in the molecular weight range from 5,000 upwards,
  (ii) It has the property of dissolving fibrin but does not activate plasminogen, trypsinogen and chymotrypsinogen.
  (iii) It is non-dialysable.
  (iv) It is a protein.
  (v) At pH 7.4 it behaves as an anion; and fibrinolytically active derivatives thereof.

Several such substances which for the sake of convenience are to be referred to in the following collectively as "cholelysin" and which all have in common the above and other properties can be recovered from human and mammalian bile. They differ from one another inter alia in respect of molecular weight. Some may be fibrinolytically active break-down products of higher molecular weight active forms. Some may also be associated active forms of lower molecular weight active forms.

It was found that these active substances occurring in bile can be precipitated with acid, more particularly, by addition of HCl to a pH of below 3.0. At least part of such precipitate can be reconstituted in buffer at pH 10.0.

The preferred fractions have a molecular weight between 5,000 and 50,000. They also have caseinolytic activity.

These fractions can be concentrated at the interphase between a chloroform/methanol partition system and are substantially insoluble in either phase and in that test retain approximately 4% of their lytic activity after having been kept in the system at 4° C for 3 weeks, will retain most of the activity when immediately removed and will retain approximately one-third of the activity when thus kept for between about 1 and 3 hours.

Because of the tendency of such enzymes to form associated active forms of high molecular weight, the upper molecular weight limit is not very important for as long as the active substance is reasonably water soluble.

Nevertheless it can be stated that some of the preferred active substances (e.g., from the point of view of purification) had molecular weights between 5,000 and 20,000, more particularly between 7,000 and 15,000 as determined by exclusion chromatography, mostly from 9,000 to 12,000. One such substance, however had a molecular weight of 7500 and another of 50,000.

The preferred substances or fractions in addition have anticoagulant properties, more particularly at least in part based on inhibition of platelet aggregation by collagen and preferably also by adenosine diphosphate (as measured in a platelet aggregometer).

Cholelysin appears to represent about 5% of the total proteins in bile and no marked differences have been observed between cholelysin recovered from different sources, e.g., humans and different mammals.

Like most proteins cholelysin can be precipitated at low temperature with alcohol or acetone.

Regarding coagulant properties the partial thromboplastic time with kaolin and one-stage prothrombin time (both determined in conventional manner) were unaffected by cholelysin.

Cholelysin breaks down fibrin into breakdown products different from those produced by plasmin.

Cholelysin can be stabilized by $Ca^{++}$ and $Mg^{++}$, e.g., in the form of their chlorides. Cholelysin has to date been identified in human bile and in the bile of baboons, cattle, pigs and rats. The highest values of fibrinolytic activity in whole bile yet found were in specimens of bovine bile taken from the gall-bladder.

It is preferably provided as a natural component of bile in a form at least 10 times, preferably at least 100 times as concentrated as in average human bile. Preferably it is sufficiently purified to form substantially a single peak when chromatographed by exclusion chromatography or ion exchange chromatography, preferably both.

Also in accordance with the invention there is provided a process for preparing a fibrinolytic substance which comprises separating from bile a proteinaceous fraction having fibrinolytic activity.

Preferably such process comprises concentrating or isolating cholelysin from bile by rendering said choleysin insoluble in bile by the addition of a protein insolubilising agent. In this context it is pointed out that the total protein content of bile is only approximately 0.15 by weight, which means that mere precipitation of all proteins will already result in a very substantial concentration as compared with the concentration of cholelysin in ordinary bile. A preferred precipitant which simultaneously appears to act as a stabilizer for cholelysin is ammonium sulphate which for substantially complete precipitation is preferably employed in a concentration of between about 12 and 33%, depending on the characteristics of the batch of bile used. On the average complete recovery is obtained with about 26% by weight of ammonium sulphate. Advantageously the precipitates may be further purified by chromatography, preferably by exclusion chromatography and/or ion exchange chromatography, preferably both.

If desired purification by other methods based on molecular size, shape and charge, e.g., isoelectric focussing, electrodialysis and/or ultracentrifugation may also be resorted to.

In the preferred process the step of separating the cholelysin from bile is preceded by a step of removing bile acids from said bile. This may be achieved by ion exchange.

In accordance with a further aspect of the invention there is provided a method of dissolving fibrin which comprises subjecting such fibrin to the lytic action of a composition comprising a fibrinolytic substance in accordance with the invention (cholelysin) as hereinbefore. Also there is provided a method of inhibiting coagulation of blood which comprises incorporating in such blood a coagulation inhibiting concentration of such substance.

The scope of the invention extends to these methods when carried out in vitro and in vivo.

Furthermore the invention includes a pharmaceutical preparation comprising a fibrinolytically effective and/or platelet aggregation inhibiting concentration of a substance in accordance with the invention as hereinbefore defined in a physiologically compatible form, preferably in intravenously administrable form.

Preferably the preparation is one for the treatment of thrombosis, and preferably it is provided in the form of dosage units. The preparation may be in a form suitable for intravenous injection or by administration in drip form.

When in the form of dosage units, e.g., ampoules for injection, the dosage units may for example be between 1 and 50 mg, preferably between 5– 30 mg, say 25 mg when used for humans. When administered by drip the rate of administration may be between 1 and 50, say 25 mg/hr.

The half life of cholelysin in vivo is about one-half hour (in rats).

At the concentration levels aforesaid the only observable physiological effect was a drastically prolonged bleeding time.

The combined presence of anticoagulant and fibrinolytic properties can be used to dissolve clots already formed and to prevent formation of new clots or to weaken any clots that may still form. The pharmaceutical preparations may include a suitable excipient or carrier and may preferably be stabilized.

The scope of the invention is also intended to include preparations wherein cholelysin is combined with other active substances, e.g., substances which inhibit the clotting of blood, including the substances referred to in the introduction to this specification, or other substances which either themselves have fibrinolytic activity or which promote fibrinolysis in vivo.

Cholelysin may also in appropriate cases be administered in conjunction with other drugs to counteract possible thrombogenic side effects of such drugs.

DESCRIPTION OF PREFERRED EMBODIMENTS

In the following the invention will be further elucidated by way of example, partly with reference to the accompanying drawings.

In the drawings:

FIG. 1 illustrates the fibrinolytic activity of whole human bile and stability of such activity at different temperatures;

FIG. 2 represents an ion exchange chromatogram of the ammonium sulphate precipitate of ox bile;

FIG. 3 represents an exclusion chromatogram of the ammonium sulphate precipitate of ox bile.

EXAMPLE 1

Referring to FIG. 1: Pooled bile from four patients was diluted 1/20 with Tris/NaCl buffer (Tris 0.06 M and NaCl 0.09 M with azide 0.02%, pH 7.5. This buffer was used for all dilutions and for elution in all column chromatography. Samples were preincubated in a water bath at the temperatures indicated. Following preincubation for the indicated time, 25 $\mu$l aliquots were applied in duplicate to a fibrin plate. Incubation of the fibrin plate was carried out for 24 hours in a chamber saturated with water vapor, and the zones of lysis were measured along two diameters at right angles to each other. The calculated areas were averaged and expressed in mm$^2$. Plasmin in 50% glycerol was stored at −40° C and used as a control in all experiments. Twenty-five $\mu$l of a plasmin solution containing 0.1 CTA units per ml gave a zone of lysis of 180 ± 20 mm$^2$.

EXAMPLE 2

100 ml ox bile intimately mixed for 30 minutes at 25° C with 3 g ion exchanger (DEAE Sephadex A50) to remove the bile acids. The mixture was centrifuged for 30 minutes at 15,000 r.p.m. The sediment was washed with 50 ml Tris HCl buffer pH 3.0 with centrifugation and discarded.

The combined supernatants were diluted with buffer to a volume of 100 ml, to which 40% w/w of ammonium sulphate were added. The mixture was centrifuged at 4° C at 15,000 r.p.m. The supernatant was discarded.

The sediment was redissolved in Tris HCl buffer pH 8.5, purified by dialysis against Tris HCl buffer pH 8.5.

Samples of the solution so obtained were then chromatographed as follows:

Proteolytic activity for both ion exchange and molecular exclusion chromatography was followed by measuring the area (mm$^2$) lysed in 17 hrs on a fibrin plate at 37° C, by each fraction collected.

ION EXCHANGE CHROMATOGRAPHY

Ion exchange chromatography was carried out at 4° C using Whatman DE 32 in a column 1.5 × 45 cm and eluted with Tris buffer 0.006 M pH 8.5 and a sodium chloride gradient.

Chromatography of the ammonium sulphate precipitate of bile gave the elution profile shown in FIG. 2.

Rechromatography showed that peaks I and III were relatively chromatographically homogeneous, while II and IV consisted of several enzymes.

DETAILS OF PROCEDURE

Sample: 21 ml dialyzed DEAE, ammonium sulphate precipitate
Flow: 28 ml/hr
Resin: DEAE Cellulose
Column: 1.5 × 45 cm
Gradient: 0.006 – 0.2 M NaCl in 0.006 M Tris pH 8.5.
The dotted line in FIG. 2 represents lysis, the solid line represents absorbance.

MOLECULAR EXCLUSION

Separation of the ammonium sulphate precipitated bile on a G200 column gave the separation shown in FIG. 3.

DETAILS OF PROCEDURE

Sample: 2 ml DEAE ppt.
Resin: G200
Flow: 8.8 ml/hr
Fraction size: 2.2 ml
Column size: 1.5 cm × 96 cm
Buffer: 0.006 M Tris pH 8.5.

ANALYSIS OF ENZYME ACTIVITY

1. Proteolytic Activity (a) Fibrin Plate

Peaks I – IV obtained from ion exchange (FIG. 2) were pooled separately and 20 μl aliquots placed on both unheated and heated (86° C, 30 min.) fibrin plates. The plates were incubated for 17 hours at 37° C and the extent of the lysis measured in mm². The results can be seen in Table I.

TABLE I

| Sample | Expt. 1 Fibrin Plate Normal | Heated | Expt. 2 Normal | Heated |
|---|---|---|---|---|
| PEAK I | 195 | 156 | 70 | 81 |
| II | 418 | 374 | 226 | 182 |
| III | 126 | 168 | 252 | 156 |
| IV | 70 | 81 | 96 | 120 |
| DEAE A/S PPT | 3375 | 4000 | — | — |
| PLASMIN | — | — | 72 | 90 |
| HUMAN BILE | 238 | 144 | — | — |

(b) Casein Hydrolysis

Proteolytic activity by casein hydrolysis was measured by a standard procedure (Methods in Enzymology, Colowick & Kaplan) and the results shown in Table II. Crystalline trypsin and Chymotrypsin were also measured for comparison.

TABLE II
PROTEOLYTIC ACTIVITY OF BILE FRACTIONS BY CASEIN HYDROLYSIS

| ENZYME | PROTEOLYTIC ACTIVITY $\Delta A$ 280, mg prot.$^{-1}$ |
|---|---|
| CHYMOTRYPSIN | 92 |
| TRYPSIN | 35 |
| PEAK I | 9.88 |
| PEAK II | 15.63 |
| PEAK III | 20.91 (approx) |
| PEAK IV | 21.765 |

(c) Specific Substrates

The pooled ion exchange fractions were tested for their specificity towards basic amino acids using N α Benzoyl-Argenyl Ethylester (BAEE), using a method obtained from Miles Seravac (Pty) Ltd. The results appear in Table III.

TABLE III
RATE OF REACTION OF PEAKS I - IV WITH BAEE

| ENZYME | RATE OF HYDROLYSIS OF BAEE $\Delta A$ 253,min$^{-1}$, mg. prot.$^{-1}$ |
|---|---|
| TRYPSIN | 3.13 |
| PEAK I | 0.201 |
| PEAK II | 0 |
| PEAK III | 0 |
| PEAK IV | 0 |

2. Activator Activity

The four peaks obtained (I–IV) by ion exchange chromatography were tested for plasminogen activator activity. The experiment consisted of measuring the amount of casein hydrolysed by Peak I–IV in the presence and absence of plasminogen one unit/ml with urokinase 500 μ/ml as a standard. The results can be seen in Table IV. The readings were all zero.

TABLE IV
ACTIVATION OF PLASMINOGEN BY BILE PROTEASES

| REACTANTS | CASEIN HYDROLYSIS (A 280 nm) | | | |
|---|---|---|---|---|
| | I | II | III | IV |
| ENZYME + BUFFER | 0.290 | 0.589 | 0.108 | 0.475 |
| ENZYME + PLASMINOGEN | 0.339 | 0.297 | 0.094 | 0.572 |
| BUFFER + PLASMINOGEN | 0.133 | 0 | 0 | 0 |
| HYDROLYSIS DUE TO ACTIVATION | −0.074 | −0.292 | 0.014 | 0.097 |
| PLASMINOGEN & UROKINASE | 0.320 | | | |

All four fractions were stable for 5 months at 4° C in the presence of (M/40) CaCl$_2$ and Mg Cl$_2$.
Molecular weights were determined by exclusion chromatography:

| PEAK I | 10 000 | (34 μg) |
|---|---|---|
| PEAK II | 12 000 | (12 μg) |
| PEAK III | 9 500 | (32 μg) |
| PEAK IV | (50 000) | (50 μg) |
| | ( 7 500) | |

Anticoagulant and lytic effects in rat mesenteric vessels

Thrombosis was induced in a conventional manner by electric current (60 seconds) to produce a spasm, with the following results:

Control:

| Current μA | Spasm | Thrombosis | Embolism (minutes) | resolution of clot (minutes) |
|---|---|---|---|---|
| 50 | ± | 60% | 5 | 9½ |
| 100 | + | 100% | 8–00 | 15–∞ |
| 200 | + | 100% | 15–00 | ∞ |

After, administration of 25 μg cholelysin

| 50 | ± | 0 | 0 | 0 |
|---|---|---|---|---|
| 100 | + | 0 | 0 | 0 |
| 200 | + | 50% | 4–18 min. | 8–∞ |

1 Hour after injection of cholelysin

| 50 | ± | 50% | 1–5 min. | 4–6 |
|---|---|---|---|---|
| 100 | + | 100% | 1–5 min. | 4–18 |

Thrombolytic effect in rabbit

The test was carried out by a known technique of artificially inducing thrombosis with phenol into an occluded segment of the femoral vein of rabbits. In spite of the experimental difficulties a significant degree of prevention of thrombosis was observed.

Platelet aggregation assay

Materials:
  human plasma containing platelet to a final concentration of 200,000 per microliter.
  Saline/phosphate buffer.
  Cholelysin at strength of 400 units per ml. One unit is the amount which produces 1 mm$^2$ of lysis on fibrin plates made from 10 ml 0.1% fibrinogen solution and 0.2 ml calcium thrombin solution, gently rotated 20 times, held open at room temperature 2 hours, incubated at 37° C for 10 minutes.
  Adenosine diphosphate M$^{-5}$
  Collagen standard suspension (5 g whole tendom extracted in Waring blender to final volume of 30 ml).

Mix platelet suspension in plastic well with specified substance and stir with magnetic stirrer. Record optical density so that an upwards deflection registers increasing translucency.

Mix cholelysin with ADP or collagen to a final concentration of 40 or 80 units per ml. The inhibition is demonstrable at 40 units, and complete at 80 units.

Precipitation of cholelysin

The fractions obtained by molecular exclusion chromatography were tested for their precipitability by several precipitants.

All samples were diluted with 0.1 M phosphate buffer (pH 5.8) to a concentration of 400 units/ml.

Addition of chloropromazine to a final concentration of 10 mM precipitated all activity.

Addition of promazine or amitryptilene to a final concentration of 5 mM and 10 mM respectively precipitated (on average) about 75% of all lytic activity.

I claim:

1. A process for isolating a proteinaceous fibrinolytic caseinolytic composition derived from mammalian bile having a molecular weight range of 5,000 to 50,000, characterized by the following properties:
   (a) insolubility in aqueous ammonium sulfate,
   (b) will dissolve fibrin but not active plasminogen, trypsinogen and chymotrypsinogen,
   (c) at pH 7.4, will act as an anion,
   (d) will inhibit platelet aggregation by collogen,
   (e) insolubility in chloroform and in methanol,
which comprises adding to mammalian bile a precipitating agent for protein, thereby precipitating said proteinaceous composition.

2. A process of claim 1 wherein the precipitating agent is selected from the group consisting of water-soluble alcoholic and ketonic protein precipitating agents.

3. A process of claim 1 wherein the precipitating agent is selected from the group consisting of ethanol, acetone and ammonium sulfate.

4. A process according to claim 1 wherein there is utilized between 12 and 35% weight/weight (based on the total weight of the mixture) of ammonium sulfate.

5. A process according to claim 3 wherein prior to the precipitation step the bile is treated with an anionic ion exchange resin, and the liquid fraction separated from therefrom and utilized in the precipitation step.

6. A process according to claim 5 wherein the ammonium sulfate precipitate is purified by ion exchange chromatography.